US012088759B2

(12) United States Patent
Kakkar et al.

(10) Patent No.: US 12,088,759 B2
(45) Date of Patent: Sep. 10, 2024

(54) VULNERABLE CALLEE MONITORING SYSTEM

(71) Applicant: Optum, Inc., Minnetonka, MN (US)

(72) Inventors: Saloni Kakkar, New Delhi (IN); Ramprasad Anandam Gaddam, Mumbai (IN); Gregory J. Boss, Saginaw, MI (US)

(73) Assignee: Optum, Inc., Minnetonka, MN (US)

( * ) Notice: Subject to any disclaimer, the term of this patent is extended or adjusted under 35 U.S.C. 154(b) by 342 days.

(21) Appl. No.: 17/645,692

(22) Filed: Dec. 22, 2021

(65) Prior Publication Data

US 2023/0199112 A1  Jun. 22, 2023

(51) Int. Cl.
*H04M 3/42* (2006.01)
*G16H 10/60* (2018.01)
*G16H 40/67* (2018.01)
*H04W 4/029* (2018.01)

(52) U.S. Cl.
CPC ........ *H04M 3/42357* (2013.01); *G16H 10/60* (2018.01); *G16H 40/67* (2018.01); *H04W 4/029* (2018.02); *H04M 2250/60* (2013.01)

(58) Field of Classification Search
CPC ......... H04M 3/42357; H04M 2250/60; H04M 3/42195; H04M 2203/551; H04M 2203/556; H04M 2203/651; H04M 2250/12; H04M 3/42093; G16H 10/60; G16H 40/67; G16H 40/20; G16H 40/63; G16H 50/70; G16H 50/30; H04W 4/029; H04W 12/08; H04W 4/38; H04W 4/90; H04L 63/101

See application file for complete search history.

(56) References Cited

U.S. PATENT DOCUMENTS

| 8,918,089 B2 | 12/2014 | Chavernac |
| 9,451,083 B1 | 9/2016 | Eda et al. |
| 10,129,366 B2 | 11/2018 | Agarwal et al. |
| 10,397,400 B2 | 8/2019 | Gupta et al. |
| 11,102,304 B1 * | 8/2021 | Jain .......................... H04L 67/12 |
| 2015/0172441 A1 | 6/2015 | Samhat |
| 2015/0288797 A1 * | 10/2015 | Vincent .................. G16H 10/60 |
| | | 455/404.2 |
| 2017/0300655 A1 * | 10/2017 | Lane ...................... G16H 10/60 |
| 2020/0129808 A1 * | 4/2020 | Fomin ................ A63B 24/0062 |

(Continued)

FOREIGN PATENT DOCUMENTS

KR  100587419 B1  6/2006

OTHER PUBLICATIONS

US 10,356,250 B2, 07/2019, Mehta et al. (withdrawn)

(Continued)

*Primary Examiner* — Sharad Rampuria
(74) *Attorney, Agent, or Firm* — Shumaker & Sieffert, P.A.

(57) ABSTRACT

A method comprising: monitoring, by a computing system, a callee device for missed phone calls from a caller; determining, by the computing system, based on a behavioral history of the callee, callee health parameters of the callee, and a number of the missed phone calls from the caller, whether an unresponsiveness condition is satisfied; and based on a determination that the unresponsiveness condition is satisfied and in response to a missed phone call from the caller, causing a caller device to present callee health data to the caller.

18 Claims, 9 Drawing Sheets

(56) References Cited

U.S. PATENT DOCUMENTS

2022/0059236 A1* 2/2022 Madan .................. G16H 40/63
2023/0107712 A1* 4/2023 Gil ........................ G16H 20/70
700/28

OTHER PUBLICATIONS

Kristiansen, Lill. "Nurse calls via personal wireless devices; some challenges and possible design solutions." 2011 24th International Symposium on Computer-Based Medical Systems (CBMS). IEEE, 2011. (Year: 2011).*
Ahmad, Raja Wasim, et al. "Blockchain-based forward supply chain and waste management for COVID-19 medical equipment and supplies." IEEE Access 9 (2021): 44905-44927. (Year: 2021).*
Rotter et al., "16 emergency apps for wildfires, earthquakes and other disasters," CNET, accessed from https://www.cnet.com/home/energy-and-utilities/16-emergency-apps-for-wildfires-earthquakes-and-other-disasters/, May 29, 2021, 9 pp.

* cited by examiner

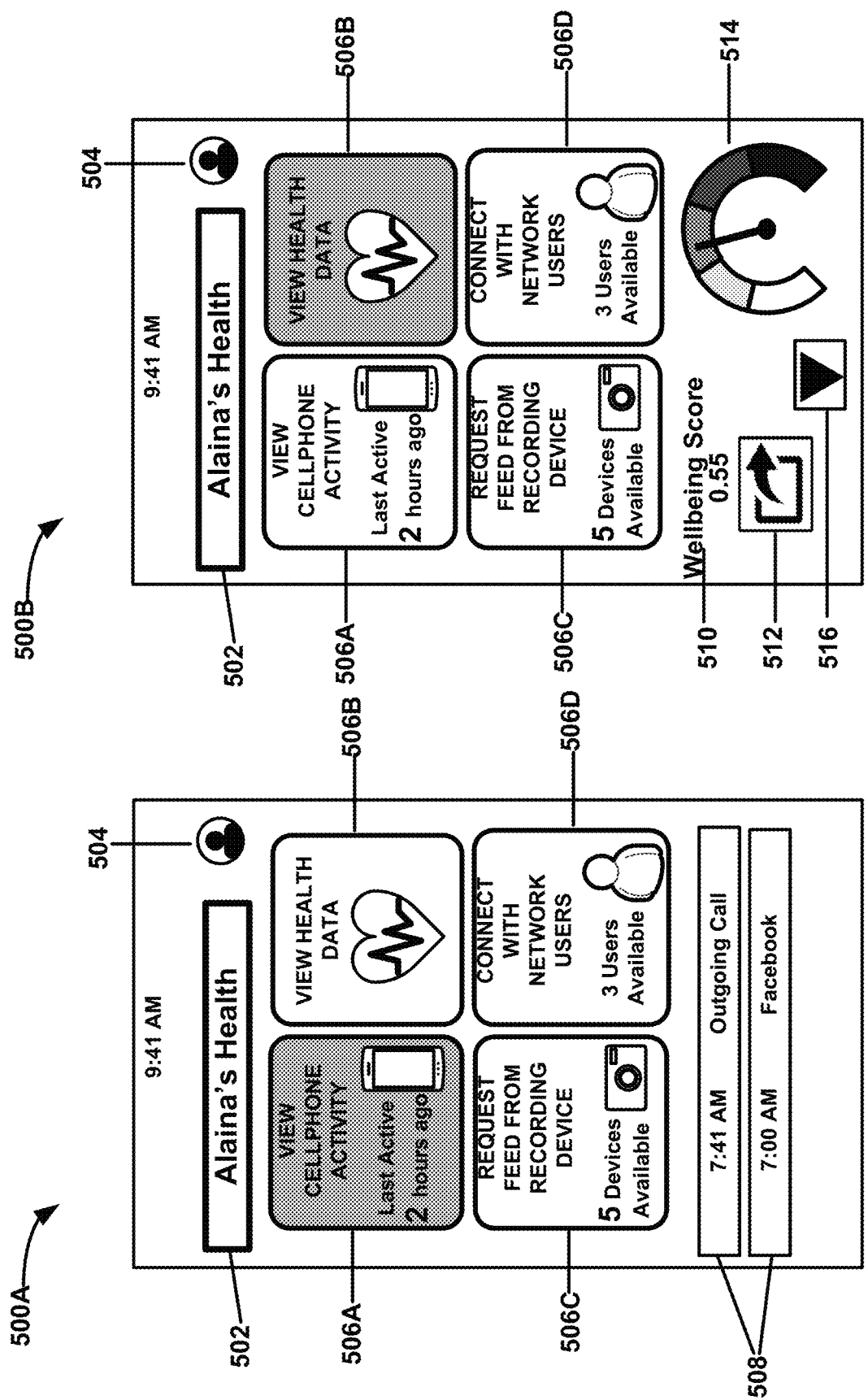

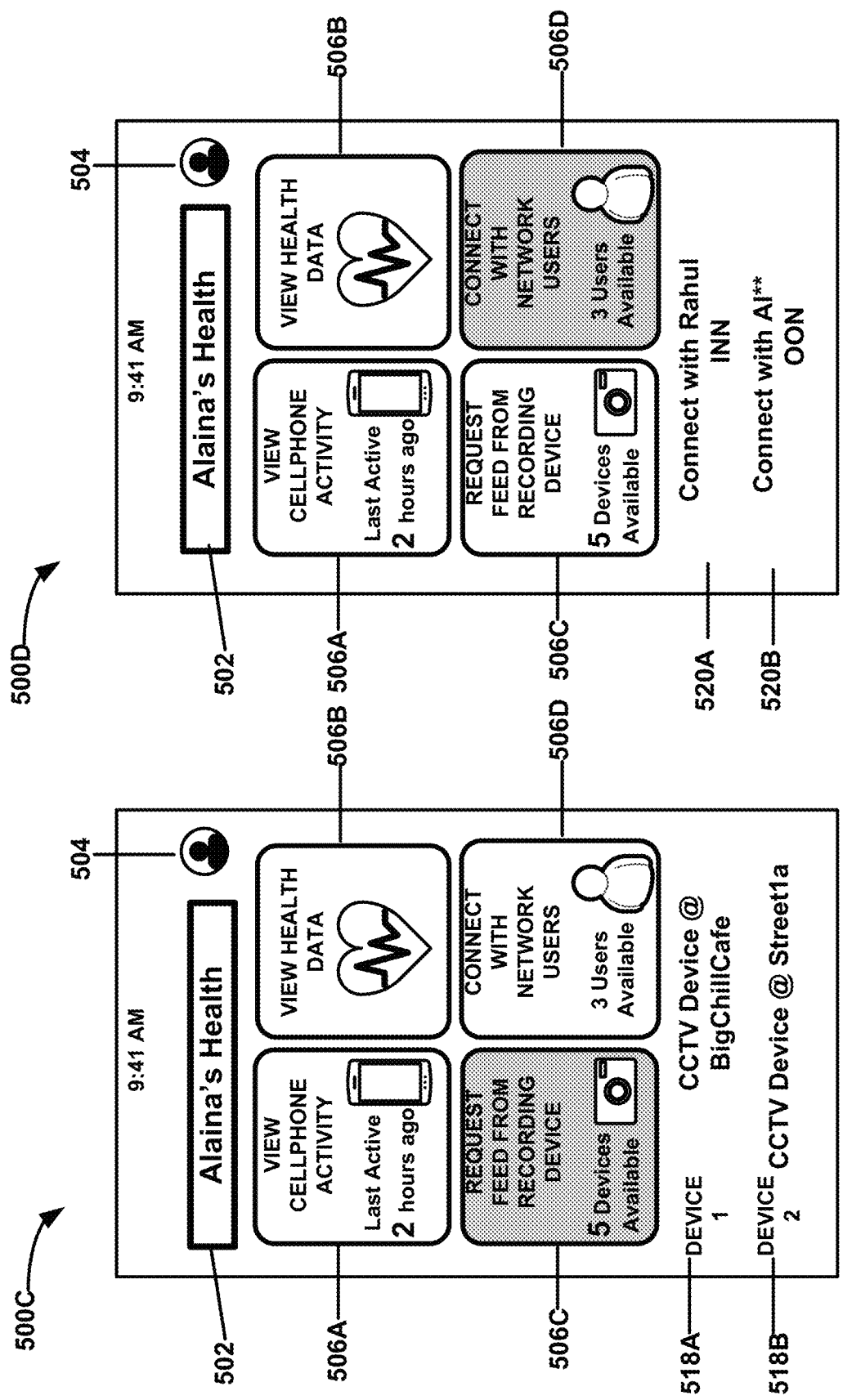

VULNERABLE CALLEE MONITORING SYSTEM

TECHNICAL FIELD

The disclosure relates to health and communications monitoring techniques.

BACKGROUND

Many people may have conditions (e.g., medical conditions, age, disabilities) that would render them vulnerable and may require additional care. In some cases, these conditions may make it difficult for the vulnerable people to answer calls or call for aid. Friends, family members, physicians, and/or other parties may want to verify the status of the vulnerable individuals when they cannot reach the individual.

SUMMARY

In general, the present disclosure describes devices, methods, systems, and techniques for monitoring the health status of a vulnerable callee. According to some aspects of this disclosure, a computing device and/or system may determine whether the status of the vulnerable callee satisfies an unresponsiveness condition and may send information to a caller, recording devices, and network users to assist in ascertaining the status of the callee and provide assistance to the callee.

In some examples, this disclosure describes a method comprising monitoring, by a computing system, a callee device for missed phone calls from a caller; determining, by the computing system and based on a behavioral history of the callee, callee health parameters of the callee, and a number of the missed phone calls from the caller, whether an unresponsiveness condition is satisfied; and based on a determination that the unresponsiveness condition is satisfied and in response to a missed phone call from the caller, causing a caller device to present callee health data to the caller.

In other examples, this disclosure describes a computing system comprising a memory configured to store callee health parameters; and one or more processors implemented in circuitry, the one or more processors configured to: monitor a callee device for missed phone calls from a caller; determine, based on a behavioral history of the callee, the callee health parameters, and a number of the missed phone calls from the caller, whether an unresponsiveness condition is satisfied; and based on a determination that the unresponsiveness condition is satisfied and in response to a missed phone call from the caller, cause a caller device to present callee health data to the caller.

In other examples, this disclosure describes a non-transitory computer readable medium comprising instructions that, when executed, cause processing circuitry within a computing system to monitor a callee device for missed phone calls from a caller; determine, based on a behavioral history of the callee, callee health parameters of the callee, and a number of missed calls from the caller, whether an unresponsiveness condition is satisfied; and based on a determination that the unresponsiveness condition is satisfied and in response to a missed phone call from the caller, cause a caller device to present callee health data to the caller.

The details of one or more examples are set forth in the accompanying drawings and the description below. Other features, objects, and advantages will be apparent from the description and drawings, and from the claims.

BRIEF DESCRIPTION OF DRAWINGS

Reference is made to the attached drawings, wherein elements have the same reference numeral designations represent similar elements throughout.

FIG. 5 is an example user interface displayed on a caller device when the caller selects a "View Cellphone Activity" feature, in accordance with one or more techniques of this disclosure.

FIG. 6 is an example user interface displayed on the caller device when the caller selects a "View Health Data" feature, in accordance with one or more techniques of this disclosure.

FIG. 7 is an example user interface displayed on the caller device when the caller selects a "Request Feed from Recording Device" feature, in accordance with one or more techniques of this disclosure.

FIG. 8 is an example user interface displayed on the caller device when the caller selects a "Connect with Network Users" feature, in accordance with one or more techniques of this disclosure.

DETAILED DESCRIPTION

The disclosure generally describes systems and methods to monitor a communications device of a callee to determine if an unresponsiveness condition is satisfied and to send callee health data to a caller device of a caller if there is a determination that the unresponsiveness condition is satisfied. Whether the unresponsiveness condition is satisfied may depend on the behavioral history of the callee, callee health parameters of the callee, and a number of the missed calls from the caller.

Certain individuals may have physical and/or mental conditions (e.g., age, illness, disabilities) that may place them at a greater risk of harm. This disclosure describes systems and methods to monitor a communications device (callee device) of a callee and determine if the callee is unresponsive (e.g., by determining if an unresponsiveness condition is satisfied) and may require assistance. The techniques of this disclosure may account for the specific situation of the callee by accounting for the behavioral history of the callee (e.g., when callee may be unavailable to communicate with caller), callee health parameters of the callee (e.g., the current health of the callee, pre-existing conditions and/or disabilities of the callee), and the number of missed calls from the caller (e.g., callee has missed 10 phone calls within the last two hours). In some examples, the systems and methods of this disclosure may send information, including callee health data, callee behavioral history, and/or callee activity history, to the caller to inform caller of the current conditions of the callee. In some examples, the systems and methods of this disclosure may connect caller with one or more recording devices and network users to facilitate an evaluation of the status of the callee.

Figure 1:
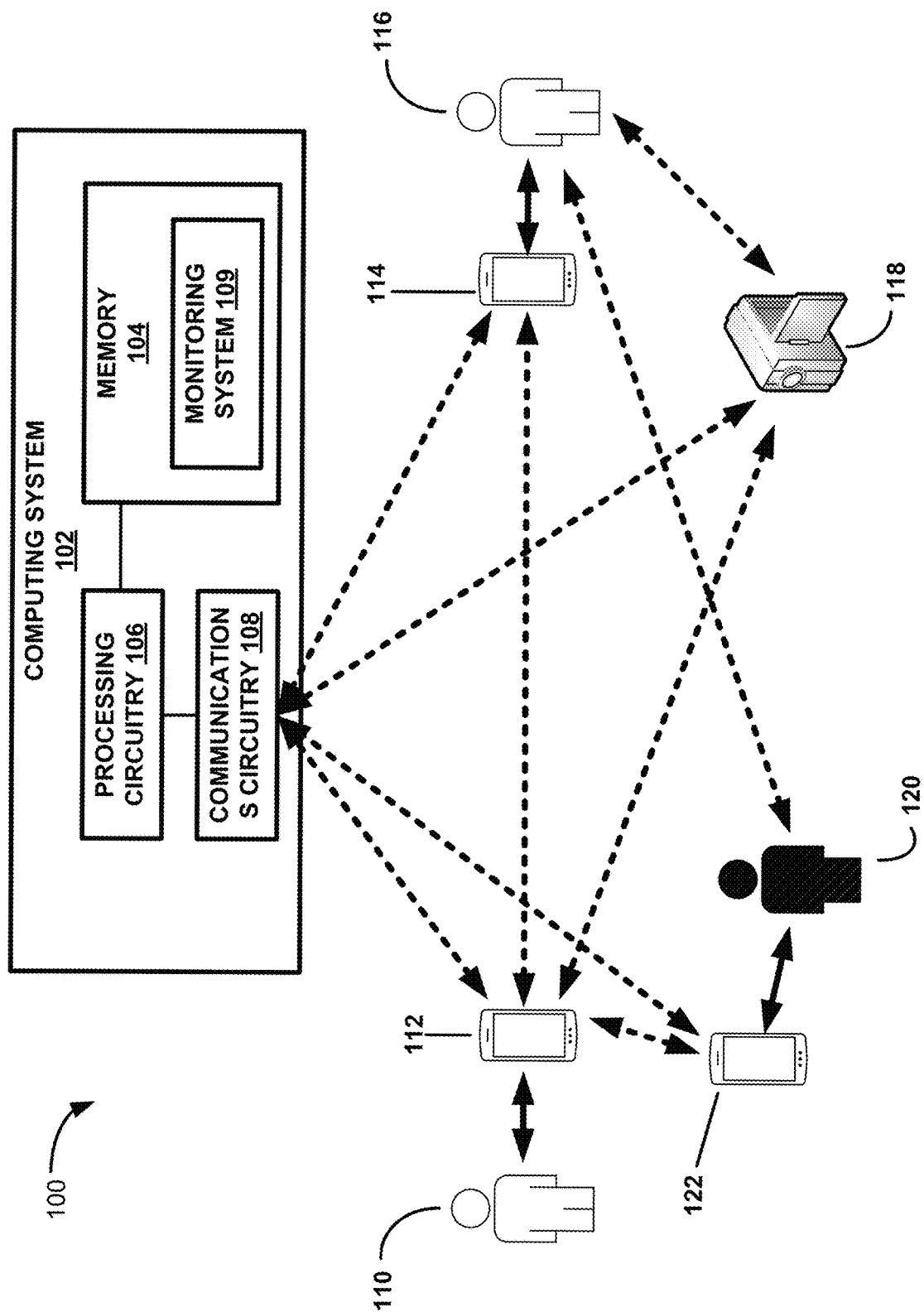
FIG. 1 is a conceptual diagram illustrating an example callee monitoring system including a computing system configured to communicate information between a caller, a callee, a network user, and a recording device, in accordance with one or more techniques of this disclosure.

FIG. 1 is a conceptual diagram illustrating an example callee monitoring system 100 including a computing system 102 configured to communicate information between a caller device 112, a callee device 114, a network user device 122, and a recording device 118.

Computing system 102 may contain components including processing circuitry 106, memory 104, and communications circuitry 108. While computing system 102 illustrated in FIG. 1 only includes memory 104, processing circuitry 106, and communications circuitry 108, another example computing system may include additional components (e.g., control circuitry, arithmetic and logic circuitry). The additional components may be configured to perform at least some of the techniques disclosed herein. Memory 104, processing circuitry 106, and communications circuitry 108 may communicate with each other. In some examples, computing system 102 may be a single computing device. In other examples, computing system 102 may be one or more computing devices (e.g., caller device 112, callee device 114, a separate computing device). In other examples, computing system 102 may be a cloud computing system.

Processing circuitry 106 may comprise circuitry configured to perform processing functions. For instance, processing circuitry 106 may include one or more microprocessors, application-specific integrated circuits (ASICs), field-programmable gate arrays (FPGAs), or other types of processing circuitry. In some examples, processing circuitry 106 of computing system 102 may read and may execute instructions stored by memory 104. Processing circuitry 106 may include fixed-function processors and/or programmable processors. Processing circuitry 106 may be included in a single device or distributed among multiple devices.

Communications circuitry 108 may enable computing system 102 to send data to and receive data from one or more other computing devices (e.g., via a communications network, such as a local area network or the Internet). In some examples, communications circuitry 108 may include wireless transmitters and receivers that enable computing system 102 to communicate wirelessly with other computing devices. Examples of communication circuitry 108 may include network interface cards, Ethernet cards, optical transceivers, radio frequency transceivers, or other types of devices that are able to send and receive information. Other examples of such communication units may include BLUETOOTH™, 3G, 4G, 5G, and WI-FI™ radios, Universal Serial Bus (USB) interfaces, etc. Computing system 102 may use communication circuitry 108 to communicate with one or more other computing devices or systems, such as client device 104. Communication circuitry 108 may be included in a single device or distributed among multiple devices.

In the example of FIG. 1, computing system 102 may communicate with a caller device 112 of a caller 110, a callee device 114 of callee 116, a recording device 118, and a network user device 122 of a network user 120. Computing system 102 may receive data from the connected devices (e.g., callee device 114, one or more biometric devices (not pictured), etc.). Memory 104 may store data received from the connected devices.

Processing circuitry 106 may read instructions from memory 104 and may execute instructions stored by memory 104. Execution of the instructions by processing circuitry 106 may configure or cause computing system 102 to provide at least some of the functionality ascribed in this disclosure to computing system 102. Memory 104 may be included in a single device or distributed among multiple devices.

As shown in the example of FIG. 1, memory 104 may include computer-readable instructions associated with a monitoring system 109. Execution of instructions associated with monitoring system 109 may configure or cause computing system 102 (e.g., processing circuitry 106, communications circuitry 108, etc.) to perform particular actions. For ease of explanation, this disclosure may describe monitoring system 109 as performing actions when processing circuitry 106 executes the computer-readable instructions of monitoring system 109.

In some examples, monitoring system 109 is implemented at least partially in caller device 112, callee device 114, and/or computing system 102. For example, some instructions associated with monitoring system 109 may be executed by processing circuitry of caller device 112, callee device 114, and/or computing system 102. Thus, discussion in this disclosure of certain actions performed by monitoring system 109 may be performed by one callee device 112, callee device 114, or computing system 102.

In some examples, monitoring system 109 may obtain a behavioral history of callee 116, e.g., from callee device 114. In some examples, monitoring system 109 may determine the behavioral history of callee 116 based on callee 116 input (e.g., through a survey). Monitoring system 109 may also receive data on the callee health parameters, e.g., from callee device 114 and/or one or more biometric devices (not pictured) (e.g., an implantable medical device, an external biometric monitoring device). Monitoring system 109 may also receive data from callee device 114 indicating the number and frequency of missed calls from caller device 112 or any other device corresponding to caller 110.

In some examples, monitoring system 109 may also obtain data on the callee health parameters from callee device 114 and/or one or more biometric devices (not pictured) (e.g., an implantable medical device, an external biometric monitoring device). In some cases, monitoring system 109 may determine the callee health parameters based on callee 116 input. In another example, callee device 114 may automatically receive the blood pressure of the callee 116 from a blood pressure monitor and automatically transmit the blood pressure value to monitoring system 109.

As monitoring system 109 receives data, monitoring system 109 may determine whether an unresponsiveness condition for callee 116 is satisfied. Monitoring system 109 may determine whether the unresponsiveness condition for callee 116 is satisfied based on the behavioral history of callee 116 and the callee health parameters of callee 116. For example, monitoring system 109 may determine that the unresponsiveness condition for callee 116 is satisfied if callee 116 does not answer five calls from caller 110 within one hour. In some examples, monitoring system 109 may determine that the unresponsiveness condition for callee 116 is satisfied if monitoring system 109 determines that the current callee behaviors, compared to the behavioral history of callee 116, and the callee health parameters of callee 116 exceed an outlier activity threshold. Monitoring system 109 analyzes the data to determine a normal range of behaviors for callee 116 and a range of behaviors that exceed the outlier activity threshold. The outlier activity threshold may include the types of behavior that may be considered abnormal and/or risky for callee 116. In other examples, monitoring system 109 may also determine a callee health parameters baseline and/or a callee 116 wellbeing score using the data received by monitoring system 109.

Once monitoring system 109 determines whether the unresponsiveness condition for callee 116 is satisfied, monitoring system 109 may store data in memory 104 indicating whether the unresponsiveness condition for callee 116 is satisfied.

If monitoring system 109 determines that the unresponsiveness condition for callee 116 is satisfied, monitoring system 109 may send callee status information to caller device 112. The callee status information may include callee health data, the activity history of callee device 114, and/or the behavioral history of callee 116. Callee health data may include data measured during the period of time around the missed calls. The callee health data received by caller device 112 may only include callee health parameters that callee 116 has authorized caller 110 to receive. For example, callee device 114 or another device of callee 116 may receive indications of user input from callee 116 to authorize caller 110 to receive blood pressure data but not breathing rate data. In other examples, caller device 112 may also receive the wellbeing score of callee 116 in addition to or instead of callee health data.

Activity history of callee device 114 may include the number of calls made by (outgoing calls), successfully received by (picked up incoming calls), or missed by callee device 114. Activity history of callee device 114 may include a timestamp corresponding to each activity. Activity history of callee device 114 may also include application data indicating the use and corresponding timestamp of one or more applications installed on callee device 114. The applications may include, but are not limited to, social media applications (e.g., Facebook, Twitter, Reddit, Instagram), online streaming applications (e.g., Netflix, HBOMax), or medical-related applications. Behavioral history of callee 116 may include calendar information of callee 116, Do-Not-Disturb periods recorded by callee device 114, or routines of callee 116 recorded by callee 114.

In some examples, monitoring system 109 may only communicate a fraction of the authorized information to caller 110 and communicate increasing amounts of authorized information as callee 116 remains unresponsive. For example, monitoring system 109 may initially only send the activity history of callee device 114 to caller device 112 when the computing system 102 determines that the unresponsiveness condition is satisfied but may then send callee health data and/or callee wellbeing score to caller device 112 when the unresponsiveness condition remains satisfied after 30 minutes.

While system 100 illustrates a single caller device 112 interacting with computing system 102 and callee device 114, in other examples there may be a plurality of caller devices and each may communicate with the other elements of system 100 independently and monitoring system 109 may authorize each caller device to receive different callee status information than one or more of the other caller devices.

Once caller device 112 receives callee status information from monitoring system 109, caller device 112 may then connect with recording device 118 and/or network users 120 through caller device 112. Connecting with recording device 118 and/or network user 120 may include delivering a feed (e.g., audio feed, visual feed) from recording device 118 and/or network user 120 to caller device 112 and/or sending information related to callee status (e.g., location of device 114) from caller device 112 and/or computing system 102 to recording device 118 and/or network user 120. In some examples, the feed may include recorded data generated by recording device 118. In some examples, recording device 118 may transmit the feed to computing system 102 which then transmits the feed to caller device 112. Recording device 118 may include devices within a certain distance (or vicinity) of the geographical location of callee device 114 that can provide a live or recorded feed (e.g., live audio feed, live visual feed) of a nearby area to assist caller 110 in determining the condition of callee 116. The distance may depend on the availability of recording devices 118 near callee device 114. For example, if there are relatively few recording devices 118 near the location of callee device 114, monitoring system 109 may increase the distance and communicate with recording devices 118 that are farther away from callee device 114. The location of callee device 114 may be determined using Global Positioning System (GPS), signal triangulation using cell towers, approximation using the location of a connected Wi-Fi source, or other means known in the art. Recording device 118 may include Closed Circuit Television (CCTV) cameras, security cameras, mobile phones, or other similar devices. In some examples, recording device 118 may be part of an Internet of Things (IoT) system. In some examples, owners and/or operators of recording device 118 (not pictured) may have given permission to computing system 102 to use recording device 118 to assist caller 110 (or another similarly situated individual connected to computing system 102) in determining the condition of callee 116 (or another similarly situated vulnerable individual connected to monitoring system 109).

In some examples, recording device 118 may automatically accept requests for communication from caller device 112 and/or monitoring system 109 to establish a communications channel between recording device 118 and caller device 112 and transmit a live feed (e.g., audio feed, visual feed) to caller device 112. In other examples, monitoring system 109 may communicate with the owner/operator of recording device 118 and/or recording device 118 to request permission to establish a communications channel or transmit and/or receive live feeds. Monitoring system 109 may communicate information pertaining to the request, including details pertaining to caller 110 (e.g., name, relation to callee 116), or callee 116 (e.g., name, last known location, well-being information such as wellbeing score) to establish authenticity of the request for communication and transmittal. In some examples, monitoring system 109 may also establish a communications channel between caller device 112 and a communication device of an owner/operator of recording device 118 to assist in establishing authentication of request and carrying out the request. In some examples, caller device 112 and monitoring system 109 may communicate with multiple recording devices 118 simultaneously and caller device 112 may receive multiple audio and/or visual feeds from multiple recording devices 118 simultaneously. Caller device 112 may include the ability to switch between the feeds, view all feeds at the same time, view one feed at a time, view some of the feeds at a time, or combine several feeds into a single feed.

Based on the audio and/or visual feeds, caller device 112 may communicate with monitoring system 109 to update the wellbeing score and unresponsiveness condition of callee 116. Caller device 112 may indicate the presence of certain contextual clues that may be significant to monitoring system 109 to determine that the unresponsiveness condition is not satisfied. For example, caller device 112 may communicate to monitoring system 109 that, based on a visual feed from recording device 118, that callee 116 is engaged in yard work and cannot hear the ringtone from callee device 114. Caller device 112 may then communicate the contextual information to computing system 102 which may determine that, based on the contextual information, the unresponsiveness condition is not satisfied.

Caller device 112 may also connect with one or more network user devices 122. Each network user device 122 may correspond to a network user 120. Network users 120 may include individuals within a certain vicinity of the location of callee device 114 who have indicated their willingness to assist callee 116 or another similarly situated vulnerable individual ("Out of Network"). Network users 120 may be individuals previously identified by caller 110 and/or callee 116 as a "trusted contact" and is included in a callee-established network of trusted contacts ("In network"). If a trusted contact is within the certain vicinity, monitoring system 109 may prioritize connecting caller device 112 to a network user device 122 corresponding to the trusted contact when connecting caller device 112 with network user devices 122. In some examples, monitoring system 109 may initiate and/or allow caller device 112 to communicate with network user devices 122 in response to an indication that there are no recording devices 118 with which caller device 112 can communicate. In other examples, monitoring system 109 may initiate and/or allow caller device 112 to communicate with network user device 122 independent of any communications with recording devices 118.

Monitoring system 109 may provide a similar procedure to establish a communications channel between caller device 114 and network user device 122 as between caller device 114 and recording device 118. For example, monitoring system 109 may provide information pertaining to a request to communicate from caller device 114 to network user device 112 to prove the authenticity of the request to network user 120. If network user device 122 receives an indication of user input indicating that network user 120 accepts the request, monitoring system 109 and/or caller device 112 may provide information to network user device 112 that may allow network user 120 to reach the location of callee device 114. Once network user 120 has arrived at the location, network user 120 may communicate with caller device 112, monitoring system 109, and/or emergency services based on the assessment of the network user 120 of the situation. Monitoring system 109 may then update the unresponsiveness condition and/or wellbeing score of callee 116 based on feedback from caller device 112 and/or network user device 122.

Once monitoring system 109 sends callee status information to caller device 112, monitoring system 109 may also send a notification to callee device 114 indicating who monitoring system 109 has sent callee status information to and what callee status information was sent. For example, after monitoring system 109 sends callee status information containing callee heart rate and callee device location to caller device 112, monitoring system 109 may send a notification to callee device 114 indicating that monitoring system 109 has sent callee status information containing callee heart rate and callee device location to caller 110.

In some examples, callee 116 may become responsive after a certain amount of time but may be unable to reach caller 110 through caller device 112. Monitoring system 109 may send updated callee health data and/or updated wellbeing scores to caller 110 through caller device 112. In other examples, monitoring system 109 may connect callee 116 with recording device 118 and transmit an audio and/or visual feed to caller device 112. In other examples, monitoring system 109 may transmit the audio and/or visual feed to one or more other display devices (not pictured) within the vicinity of caller 110 to communicate status of callee 116 to caller 110. For example, monitoring system 109 may transmit a video feed confirming safety of callee 116 to a smart TV within a home of caller 110. In some examples, monitoring system 109 may initiate a routine with one or more IoT devices to display a pre-recorded message from callee 116 confirming safety of callee 116 to caller 110.

Figure 2:
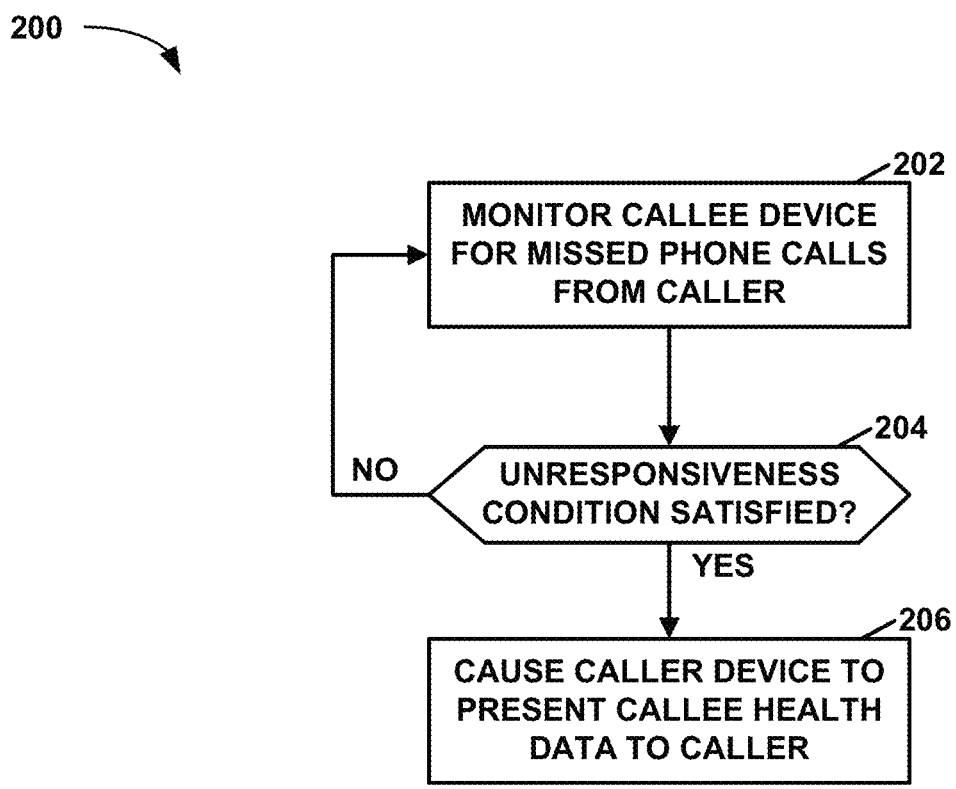
FIG. 2 is a flowchart illustrating an example callee monitoring method, in accordance with one or more techniques of this disclosure.

FIG. 2 is a flowchart illustrating an example callee monitoring method 200 in accordance with one or more techniques of this disclosure. The flowchart of FIG. 2 is described with reference to FIG. 1, however callee monitoring method 200 may be implemented by other devices.

In the example method 200 of FIG. 2, monitoring system 109 may monitor callee device 114 for missed phone calls from caller device 112 (202). Monitoring system 109 may monitor for missed phone calls by receiving data on missed phone calls from callee device 114 through communications circuitry 108, store the data in memory 104, and determine the amount of time between missed calls using processing circuitry 106. The data on missed phone calls from callee device 114 may include the identity of callers 110, the time of the each missed call, the location of callee device 114 when each phone call was missed, the number of consecutive missed calls, the amount of time between the first and last missed calls, and/or the amount of time between two consecutive missed calls. As monitoring system 109 monitors callee device 114 for missed calls from caller 110 (202), monitoring system 109 may also determine, based on the behavioral history of callee 116, callee health parameters of callee 116, and a number of missed phone calls from caller 110, whether an unresponsiveness condition is satisfied (204).

The behavioral history of callee 116 may be callee responses to one or more surveys or data from callee device 114 (e.g., calendar information, location information, application history). Behavioral history of callee 116 may comprise information on regular activities undertaken by callee 116 (e.g., work, exercise), geographic information on callee 116 (e.g., home, area callee frequently visits, areas that callee 116 rarely/never visits), and general behavioral traits of callee 116 (e.g., callee 116 normally only picks up a call from caller after the first missed call).

Callee health parameters may include health metrics or other health-related data that may be used to determine when callee 116 may be at risk and require assistance. Example callee health parameters include blood pressure, body temperature, skin temperature, heart rate, heart rate variability, resting heart rate, breathing rate, blood glucose, oxygen saturation, stress levels, pre-existing health conditions, injuries, disabilities, etc.

Monitoring system 109 may determine the unresponsiveness condition through one or more outlier detection techniques. The outlier detection techniques may include machine learning techniques or data analysis techniques (e.g., Z-score analysis). In some examples, monitoring system 109 may also factor in one or more contextual factors such as time, activity, medical conditions, or accessibility to determine the unresponsiveness condition. For example, if the missed calls occurred during the day and the location information of callee device 114 indicates that callee 116 is within the vicinity of a hospital, monitoring system 109 may determine that the unresponsiveness condition requires ten missed calls with the last 12 hours. Outlier activities by callee 116 may include a certain number of missed calls to callee device 114, the number of rings to a phone call before callee 116 picks up the call, the absence of a certain action by callee 116 (e.g., leaving callee's residence, making outbound calls through callee device 114), or cellphone activity. In some examples, monitoring system 109 may determine a wellbeing score for callee 116 in response to the missed calls from caller 110. Monitoring system 109 may first determine a callee health parameters baseline for callee 116 using the data received by monitoring system 109 from callee device 114, one or more biometric devices, callee 116, or another source. For example, monitoring system 109 may determine a baseline resting heart rate, breathing rate, and blood pressure for callee 116. Monitoring system 109 may request, using communications circuitry 108, callee health data from callee device 114 for a set period prior to and after each missed call and determine the difference between the callee health data around the missed calls and the callee health parameters baseline. The set period may include a time period around the missed calls from caller (e.g., from 30 minutes prior to the missed calls to 30 minutes after the last missed call. Monitoring system 109 may then determine a wellbeing score using a variety of factors including the callee's normal health parameters baseline, the callee health data surrounding the missed calls, health-affecting activities and contexts (e.g., exercise), existing medical conditions, and existing prescriptions. Monitoring system 109 may assign weights and numerical values to each of the variety of factors and determine a weighted wellbeing score by taking the sum of the weighted values of the variety of factors (e.g., an overall wellbeing score of 0.2). The weights may have an aggregate value of 1.

Monitoring system 109 may determine the wellbeing score by accounting for factors including a health score, location information (e.g., distance from home of callee 116, distance to a safe/unsafe location), frequently visited places, calendar information, callee device 114 sensor data, application history of an application installed on callee device 114, input from recording devices 118, and/or input from network user devices 120. In some examples, the health score may be the sum of the weighted values of a plurality of health parameters (e.g., blood pressure, body temperature, heart rate).

In some examples, monitoring system 109 may assign a wellbeing score of 0 to callee health data within the expected range of values for the callee health parameters. Wellbeing scores may provide a viewer (e.g., caller 110, callee 116, or network user 120) an approximate measurement of the current wellness of callee 116 relative to an expected wellness of the callee. In some examples, wellbeing scores may be between 0 and 1 and may indicate an amount of deviation from the expected range of values for the callee health parameters. In some examples, monitoring system 109 may provide a wellbeing label corresponding to the wellbeing score based on the wellbeing score value. For example, wellbeing scores between 0 to 0.2, 0.21 to 0.4, 0.41 to 0.6, 0.61 to 0.8, and 0.81 to 1 may be assigned wellbeing labels of "Excellent", "Good", "Average", "Poor", and "Critical", respectively. While the example wellbeing scores are between 0 and 1, any two numerical values or other representations may be used to represent the severity of the difference between the callee health data and the normal expected range of values for the callee health parameters.

In some examples, monitoring system 109 determines the unresponsiveness condition based on the wellbeing score. For example, monitoring system 109 may determine that the unresponsiveness condition is satisfied when a wellbeing score is closer to 1 (e.g., a score of 0.6) even when there are relative few missed calls and/or over a short period of time whereas computing system 102 may determine that the unresponsiveness condition is satisfied when a wellbeing score is closer to 0 (e.g., a score of 0.2) with relatively more missed calls and/or over a relatively longer period of time.

In some examples, monitoring system 109 may perform the process of determining the unresponsiveness condition in a learning mode prior to monitoring system 109 monitoring callee device 114 for missed calls from caller 110 (202). In some examples, monitoring system 109 may continue to update the unresponsiveness condition based on data received from callee device 114, one or more biometric devices, callee input, and/or other sources.

In some examples, monitoring system 109 may determine the unresponsiveness condition using an outlier activity threshold. Monitoring system 109 may determine the outlier activity threshold using the behavioral history of the callee. The outlier activity threshold may indicate the range of callee behaviors and/or callee health conditions that are within a normal, healthy range of callee activities. Any missed calls that breach the outlier activity threshold may indicate that the callee is unresponsive and/or in a vulnerable state and may require assistance. For example, if callee 116 has a habit of walking their dog three times a day, monitoring system 109 may determine that a plurality of missed calls in conjunction with the failure of callee 116 to walk their dog at all during the day is a violation of the outlier activity threshold and satisfied the unresponsiveness condition. Monitoring system 109 may determine the outlier activity threshold based on outlier activities of callee 116 that are received by monitoring system 109.

If monitoring system 109 determines that the unresponsiveness condition is not satisfied ("NO" branch of 204), monitoring system 109 may continue to monitor callee device 114 for missed calls from caller 110 (202). In some examples, memory 104 stores both the prior missed calls and any new missed calls from caller 110. Therefore, the prior missed calls from caller 100 may be included when monitoring system 109 determines whether the unresponsiveness condition is satisfied (204). In other examples, the new missed calls from caller 110 overrides prior missed calls from caller 110 that are stored in the memory 104.

If the unresponsiveness condition is satisfied ("YES" branch of 204), monitoring system 109 may cause caller device 112 to display callee health data to caller 110 (206). In some examples, monitoring system 109 only sends to caller device 112 types of callee health data that callee 116 has previously authorized to monitoring system 109 to send to callee 116. In other examples, monitoring system 109 may send to caller device 112 activity history of callee device 114 and/or behavioral history of callee 116 in addition to or in lieu of the callee health data. In some examples, monitoring system 109 may also notify callee device 114 that monitoring system 109 has caused caller device 112 to display callee health data to caller 110.

Figure 3:
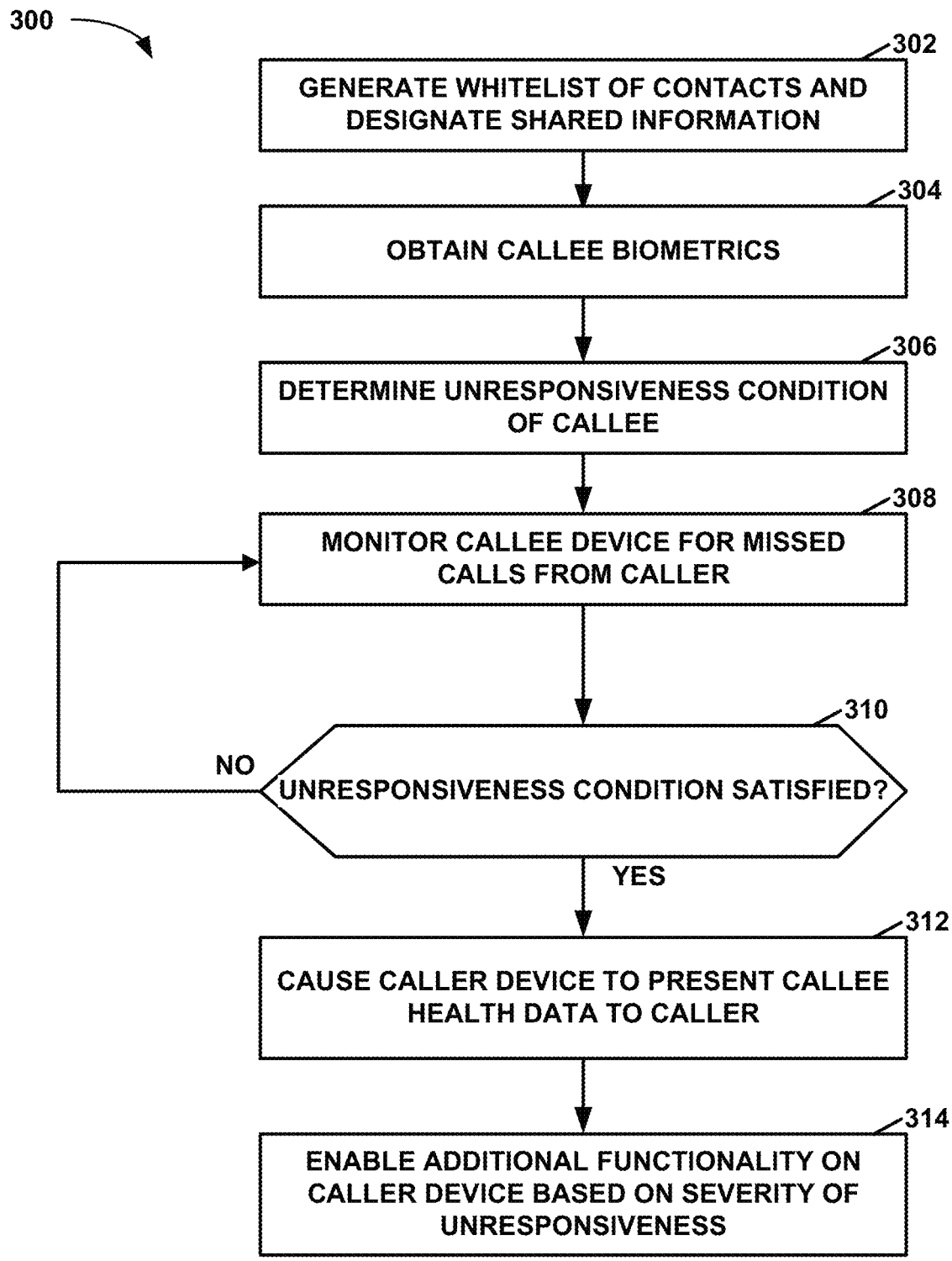
FIG. 3 is a flowchart illustrating another example callee monitoring method, including determining an unresponsiveness condition prior to monitoring a callee device for missed calls from a caller, in accordance with one or more techniques of this disclosure.

FIG. 3 is a flowchart illustrating another example callee monitoring method 300, in accordance with one or more techniques of this disclosure. The example callee monitoring method 300 is similar to example callee monitoring method 200 but a computing system (e.g., computing system 102) may generate a whitelist of contacts, obtain callee biometrics, and determine an unresponsiveness condition prior to monitoring a callee device (e.g., callee device 114) for missed phone calls from caller (e.g., caller 110).

In the example of FIG. 3, monitoring system 109 may generate, based on input from callee, a whitelist of contacts and the types of information to be shared with each contact (302). Monitoring system 109 may receive a list of contacts and the types of information that monitoring system 109 may send to caller 110 from callee device 114 and/or callee 116. The types of information that monitoring system 109 may send may include callee health parameters, callee location information, callee calendar information, sensor information from callee device 114 (e.g., camera information, microphone information, and historical information of applications installed on callee device 114. In some examples, monitoring system 109 may record designations assigned to a contact by callee 116. For example, monitoring system 109 may record that callee 116 has assigned a contact as a "trusted contact" who may be able to provide aid in times of distress. In other examples, monitoring system 109 may record that caller 110 has indicated that there are particular callees that caller 110 is concerned about or is a caretaker for.

Monitoring system 109 may also obtain callee biometrics (304). The callee biometrics may comprise callee health data corresponding to the callee health parameters and may be used to determine the unresponsiveness condition, callee health parameters baseline, outlier activity threshold, and wellbeing score. Example biometrics may include blood pressure, body temperature, skin temperature, heart rate, heart rate variability, resting heart rate, breathing rate, blood glucose, oxygen saturation, and stress levels. Monitoring system 109 may obtain biometrics through caller input, callee input, data from callee device, and/or one or more biometric devices.

Monitoring system 109 may determine an unresponsiveness condition for callee 116 (306). Monitoring system 109 may determine the unresponsiveness condition in accordance with the examples discussed in FIG. 2. In some examples, computing system 102 may also determine a callee health parameters baseline and an initial wellbeing score for callee. As monitoring system 109 continues to receive updates to callee biometrics, callee behavioral history, and other relevant date, monitoring system 109 may update the callee health parameters baseline and update the wellbeing score for callee 116 to reflect changes in callee health. Additionally, monitoring system 109 may reevaluate, based on the updated wellbeing score for callee 116, whether the unresponsiveness condition for callee 116 is satisfied.

Based on monitoring system 109 determining the unresponsiveness condition for the callee 116, monitoring system 109 may begin to monitor the callee device for missed calls from caller 112 and may determine, based on the callee behavioral history, health parameters, and number of missed phone calls, whether the unresponsiveness condition for callee 116 is satisfied (310). If the unresponsiveness condition for callee 116 is not satisfied ("NO" branch of 310), monitoring system 109 resumes monitoring callee device for missed calls from caller 110 (308). If the unresponsiveness condition is satisfied ("YES" branch of 310), monitoring system 109 may cause caller device 112 to present callee health data to caller 110 (312). In some examples, monitoring system 109 may cause caller device 112 to present additional information including callee behavioral history and callee device activity history.

Furthermore, in the example of FIG. 3, after causing caller device 112 to present callee health data, monitoring system 109 may enable additional functionalities on caller device 112 based on the severity of unresponsiveness (314). Additional functionalities may include options for caller device 112 to request communications with and feeds from recording devices 118 and/or network user devices 122. In other examples, additional functionalities may include displaying additional callee information including callee behavioral history, callee device activity history, and/or callee device location on caller device 112. Monitoring system 109 may provide caller additional options to evaluate the status of callee as the severity of unresponsiveness worsens. For example, monitoring system 109 may only initially send callee health data to caller device 112 but if callee unresponsiveness worsens (e.g., if the callee health data shows a worsening health condition), computing system 102 may enable an option to allow caller device 112 to communicate with recording devices (e.g., recording device 118) and/or network users (e.g., network user 120). In some examples, as the severity of callee unresponsiveness improves (e.g., if the callee health data shows an improving health condition), computing system 102 may remove functionalities.

Figure 4:
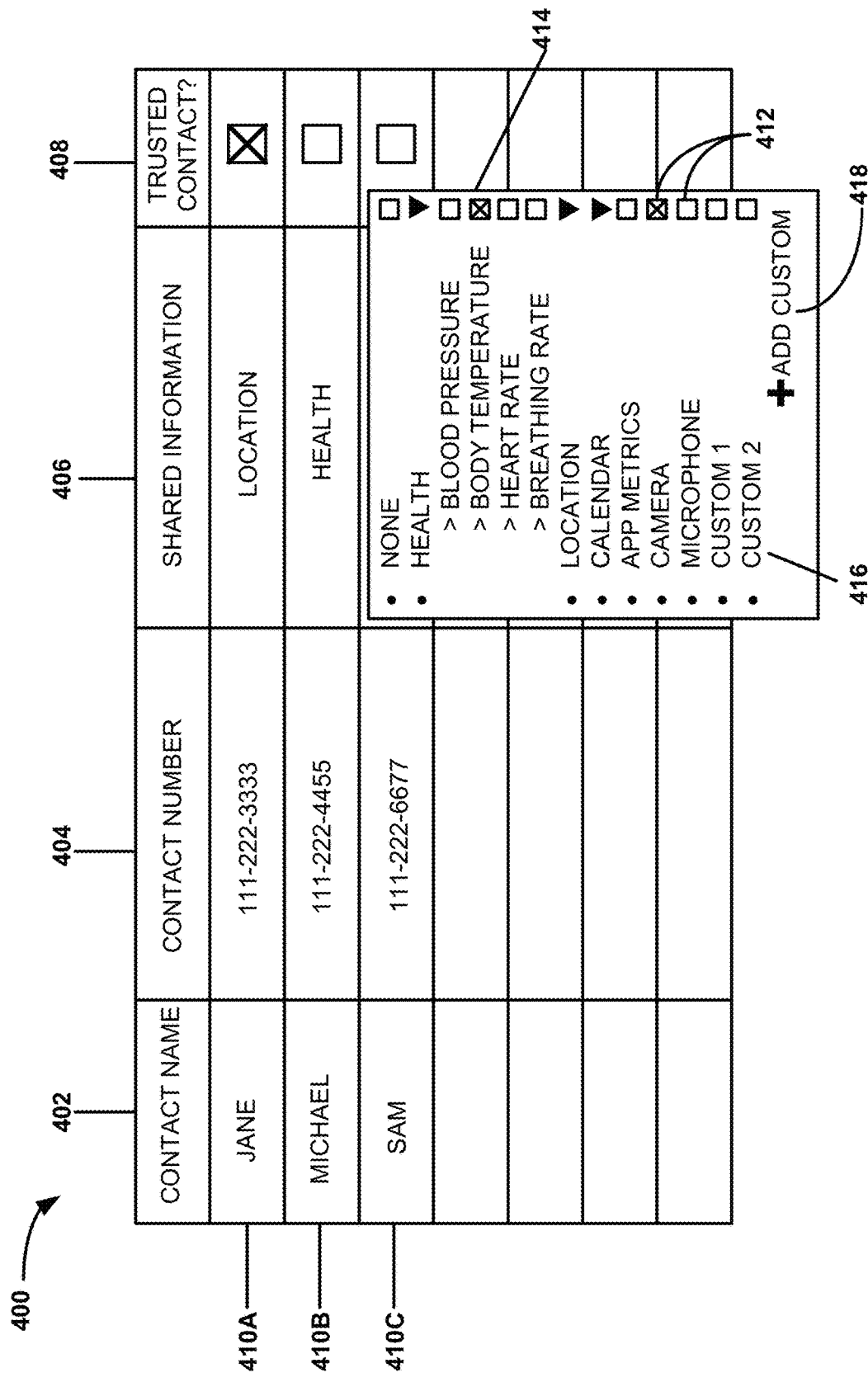
FIG. 4 is an example user interface that may be used by a callee to generate a whitelist of authorized contacts and corresponding information that a system may send when an unresponsiveness condition is satisfied, in accordance with one or more techniques of this disclosure.

FIG. 4 is an example user interface that may be used by callee 116 to generate a whitelist 400 of authorized contacts and corresponding information that a system may send when an unresponsiveness condition is satisfied, in accordance with one or more techniques of this disclosure. Whitelist 400 may include a list of authorized contacts, the authorized information that a system may send to each authorized contact person when an unresponsiveness condition is satisfied, and additional signifiers for each contact person (e.g., designating a contact person as a "trusted contact person").

In the example of FIG. 4, each authorized contact person in whitelist 400, such as Jane 410A, Michael, 410B, and Sam 410C (altogether referred to as "authorized contacts 410"), includes a contact name 402, a contact number 404, a shared information list 406, and additional designations 408 (e.g., as "trusted contact"). Contact name 402 may be manually entered by caller 110, callee 116, or other relevant party (e.g., a caretaker, a healthcare professional). In some examples, monitoring system 109 may automatically populate contact name 402 for an authorized contact person 410 using information from callee device 114, such as a contacts list or a friends list from a social media application, or one or more online accounts (e.g., a social media account). Similarly, callee 116 may enter contact number 404 for each authorized contact person 410 manually or monitoring system 109 may populate contact number 404 automatically using information from callee device 114.

For each authorized contact person 410, whitelist 400 assigns a corresponding shared information list 406. Monitoring system 109 may generate shared information list 406 based on input from caller 110, callee 116, or other relevant party (e.g., physician, healthcare worker). Shared information list 406 includes one or more of authorized categories 412. Monitoring system 109 may automatically populate shared information list 406 with a plurality of authorized categories 412 based on input from caller 110, callee 116, or other relevant party that the same plurality of authorized categories 412 is to be shared with each authorized contact person 410. For example, if monitoring system 109 receives input from callee 116 that indicates that monitoring system 109 will provide each authorized contact person 410 with the location and health information of callee 116, monitoring system 109 may automatically generate shared information lists, such as shared information list 406, containing the authorized categories 412 of "LOCATION" and "HEALTH" for each authorized contact person 410. In other examples, monitoring system 109 may populate shared information list 406 with a customized selection of authorized categories 412 based on input from caller 110, callee 116, or other relevant party. For example, monitoring system 109 may receive input from callee 116 that instructs monitoring system 109 to only share callee location information with Jane 410A and callee health information with Michael 410B. In response to input from callee 116, monitoring system 109 may populate a shared information list 406 with "LOCATION" for Jane 410A and a shared information list 406 with "HEALTH" for Michael 410B. For some of the authorized categories 412, such as "HEALTH", "LOCATION", or "CALENDAR", there may be a plurality of authorized sub-categories 414. For example, as illustrated in FIG. 4, the authorized category 412 of "HEALTH" may include the authorized sub-categories 414 "BLOOD PRESSURE", "BODY TEMPERATURE", "HEART RATE", and "BREATHING RATE." Monitoring system 109 may populate each authorized category 412 with authorized sub-categories 414 based on input from caller 110, callee 116, or other relevant party. In some examples, monitoring system 109 may populate authorized categories 412 with certain authorized sub-categories 414 based on the types of data (e.g., types of callee health data) communications circuitry 108 has received. For example, if monitoring system 109 has not received callee blood pressure data, then monitoring system 109 does not populate authorized category 412 "HEALTH" with authorized sub-category 414 "BLOOD PRESSURE"

In some examples, authorized categories 412 may include one or more custom categories 416. Callee 116, caller 110, or other relevant party may create, modify, or delete the custom categories 416. An example user interface may include an "ADD CUSTOM" option 418 which may be used to create a custom category 416. Custom categories 416 may include a plurality of the other authorized categories 412. For example, if monitoring system 109 receives input from callee 116 that authorized contact person 410 receives CUSTOM 1 information, monitoring system 109 may populate the corresponding shared information list 406 with one or more authorized categories 412 or authorized sub-categories 414 that callee 116 has selected for the CUSTOM 1 category 416. If callee 116 had selected "LOCATION" and "HEART RATE", monitoring system 109 may populate the shared information list 406 with "LOCATION" and "HEART RATE" and communications circuitry 108 may send the callee heart rate and callee device location to a device associated with the corresponding authorized contact person 410.

While the user interface of FIG. 4 uses a spreadsheet format using drop-down selections and check boxes, other graphical user interface formats may be used.

FIGS. 5-9 illustrate example user interfaces 500 A-E viewed by caller 110 when the unresponsiveness condition of callee 116 is satisfied, in accordance with one or more techniques of this disclosure. The example user interfaces 500A-E (also referred to collectively as "user interfaces 500") show what a caller may see and interact with based on the severity of callee unresponsiveness and which tiles 506A-D (also referred to as "tiles 506") caller 110 has selected on caller device 112. While user interfaces 500 utilize tiles 506, other graphical interface formats (e.g., an expandable list) may be used. In other examples, tiles 506 that may be viewed by caller 110 may differ from those illustrated in FIGS. 5-9.

Monitoring system 109 may generate user interface 500 and tiles 506 based on input from callee 116, caller 110, or other relevant party. In other examples, monitoring system 109 may determine which tiles 506 and callee information corresponding to each tile 506 may be viewed by caller 110 based on a whitelist (e.g., whitelist 400). For example, because the shared information list 406 of Jane 410A only contains "LOCATION," monitoring system 109 may generate user interface 500 that only contains tile 506A ("VIEW CELLPHONE ACTIVITY") on caller device 112 of Jane 410A. Monitoring system 109 may then only cause caller device 112 of Jane 410A to display current location and/or location history of callee device 114. In some examples, monitoring system 109 may cause a device other than caller device 112 to display user interface 500. For example, monitoring system 109 may cause a laptop, smart TV, smart watch, and/or another device to display user interface 500.

FIG. 5 illustrates an example user interface 500A displayed on caller device 112 when caller 110 selects a "View Cellphone Activity" feature (tile 506A). User interface 500A may indicate an identity 502 of callee 116 to caller 110. User interface 500A may include a login option 504. Login option 504 may allow caller 110 to log in and view user interface 500 and/or change settings of user interface 500. User interface 500A may require caller 100 to log in to view tiles 506 and callee information corresponding to each tile 506.

When caller 110 selects tile 506A, user interface 500A may highlight tile 506A to indicate that caller 100 has selected tile 506A. Tile 506A may display a time of the last recorded activity of callee device 114 ("Last Active 2 hours ago"). User interface 500A may also display, in response to caller 110 selecting tile 506A, cellphone activity history 508. Cellphone activity history 508 may include callee device 114 phone activity, such as past incoming or outgoing calls, or application activity, such as use of social media applications. Cellphone activity history 508 may include timestamps corresponding to each cellphone activity (e.g., 7:41 AM Outgoing Call). In some examples, caller device 112 may prioritize certain events within cellphone activity history 508 to display on user interface 500A. For example, caller device 112 may display the latest event of cellphone activity history 508 prior to the satisfaction of the unresponsiveness condition and/or latest communication between caller device 112 and callee device 114 before any other event within cellphone activity history 508.

FIG. 6 illustrates an example user interface 500B displayed on caller device 112 when caller 110 selects a "View Health Data" feature (tile 506B). The user interface includes identity 502 of the callee and an option 504 for caller to log in, similar to the user interface of FIG. 5. User interface 500B may highlight tile 506B to indicate that caller 100 has selected tile 506B. Caller 110 may transition from user interface 500B to any other user interface 500 (e.g., user interface 500A) by selecting the tile 506 corresponding to the other user interface 500. For example, if callee device 112 is displaying user interface 500B, caller device 112 may generate user interface 500B and caller device 112 changes to displaying user interface 500B in response to caller 110 selecting tile 506B on caller device 112. User interface 500B may display, in response to caller 110 selecting tile 506B, a wellbeing score 510, a sharing option 512, a wellbeing score graph 514 and an additional health information option 516. Another example user interface may include additional options or fewer options. Monitoring system 109 may determine wellbeing score 510 using the techniques disclosed herein.

Sharing option 512 may allow monitoring system 109 and/or caller device 112 to send wellbeing score 510, wellbeing score graph 514, and/or additional health information with a third party (e.g., a health professional). Monitoring system 109 and/or caller device 112 may send the selected information through messaging, email, social media, or other means. Monitoring system 109 may receive input from callee 116 may indicate that certain information, may not be sent or may only be sent to certain parties (e.g., family, caretaker). Based on the input from callee 116, monitoring system 109 instructs communications circuitry 108 to only send information allowed by callee 116 to third parties.

Wellbeing score graph 514 is a graphical indication of some aspect of the callee's health. In some examples, as illustrated in FIG. 5, wellbeing score graph 514 may illustrate wellbeing score 510 relative to the range of possible wellbeing scores 510. The example wellbeing score graph 514 is a gauge chart but other chart and/or graph formats may be used to illustrate wellbeing score 510. In other examples, wellbeing score graph 514 may illustrate one of more data sets within the additional health information, such as breathing rate, heart rate, and/or stress level, in addition to wellbeing score 510.

In some examples, user interface 500B may display additional health information in response to caller 110 selecting the additional health information option 516. The additional health information may include all callee health data that communications circuitry 108 has sent to caller device 112. In other examples, user interface 500B may display additional health information without requiring additional input from caller 110. User interface 500B may display additional health information in a numerical and/or graphical format.

FIG. 7 illustrates an example user interface 500C viewable by caller 110 when caller device 112 receives an indication of user input to select a "Request Feed from Nearby Devices" feature (tile 506C). User interface 500C may highlight tile 506C to indicate that caller 100 has selected tile 506C. Tile 506C may display the number of recording devices (e.g., recording device 118) that are available within the vicinity of callee device 114. If there are no available recording devices 118 within the vicinity of callee device 114, user interface 500C may indicate that 506C is not selectable by caller 110.

Once caller selects tile 506C, user interface 500C may display at least some of the available recording devices 118. For example, the user interface displays "CCTV Device @ BigChillCafe" (518A), and "CCTV Device @Street1a" (518B) (collectively referred to as "recording devices 518"). Callee device 112 may prioritize displaying recording devices 518 closest to callee device 114 or recording devices with certain functionalities (e.g., ability to transmit a visual feed) on user interface 500C. Using user interface 500B, caller 110 may be able to connect directly with the selected recording device (e.g., recording device 518A) and/or the owner/operator of the selected recording device 518A and request a transmission of an audio and/or visual feed from the recording device 518A to evaluate the status of callee 116. The name of recording device 518A on user interface 500C may identify the type of recording device 518A (e.g., CCTV) and the location of recording device 518A (e.g., at Big Chill Café). In some examples, caller device 112 may superimpose the locations of recording devices 518 on a map of the vicinity of callee device 114 for display on user interface 500C.

FIG. 8 illustrates an example user interface 500D displayed by caller device 112 when caller device 112 receives an indication of user input to select a "Connect with Network Users" feature (tile 506D). Tile 506D displays the number of network users 120 that are available within the vicinity of callee device 114. If there are no network users 520 within the vicinity of the callee device, user interface 500D may indicate that title 506D is not accessible by caller 110.

User interface 500D may also display one or more network users (Rahul 520A and Al 520B) (collectively referred to as "network users 520"). User interface 500D may provide an indication that a network user (e.g., network user 520B) is not within a callee-established network of trusted contacts ("OON" for Al 520B, where "OON" is an abbreviation for "Out of Network"). Network user 520B may an individual within the vicinity of callee device 114 who has previously indicated a willingness to assist callee 116 and/or another individual in need. User interface 500D may also provide an indication that a network user (e.g., network user 520A) is within the callee-established network of trusted contacts and is a trusted contact ("INN" for Rahul, where "INN" is an abbreviation for "In Network"). In some examples, user interface 500D may partially redact the identities of network user 520B not within a callee-established network of trusted contacts. In some examples, monitoring system 109 may prioritize displaying on user interface 500D network users 520 who are within the callee-established network of trusted contacts (e.g., if callee labels network user 520A as a "trusted contact") or network users 520 who are the closest to callee device for display on the user interface. User interface 500D may display prioritized network users 520 before any other available network users 520. User interface 500D may provide an option to request communications between caller device 112 and one or more devices corresponding to one or more available network users 520 to request the aid of network users 520 in evaluating the status of callee 116.

Figure 9:
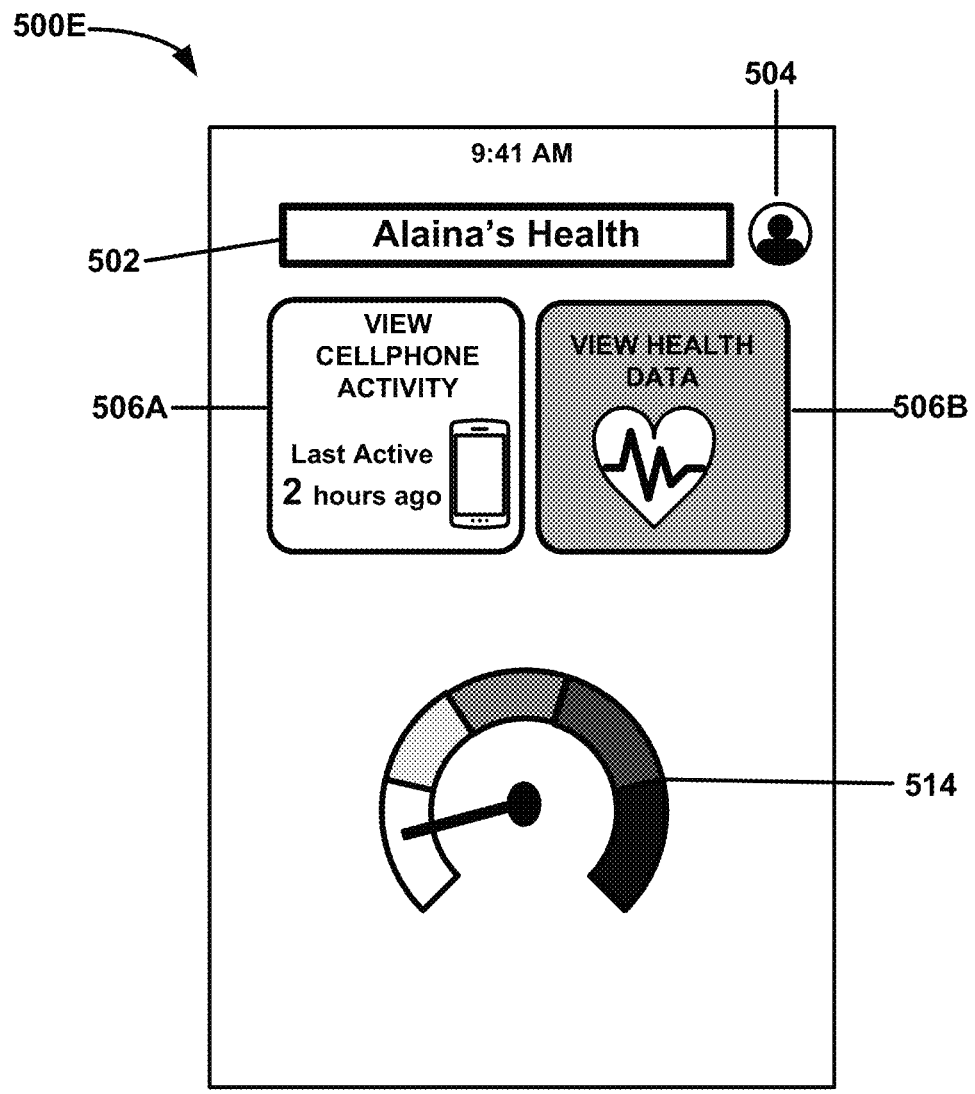
FIG. 9 is an example user interface displayed on a caller device when a computing system determines that the callee's condition is not sufficiently serious to warrant the communication of certain information to the caller, in accordance with one or more techniques of this disclosure.

FIG. 9 illustrates an example user interface 500E displayed on caller device 112 when computing system 102 determines that the condition of callee 116 is not sufficiently serious to warrant the communication of certain information to caller 110, in accordance with one or more techniques of this disclosure. As compared to the example user interfaces of FIGS. 5-8, example user interface 500E makes certain tiles 506, such as tiles 506C and 506D unavailable for access by caller 110. In some examples, as illustrated in FIG. 9, user interface 500E may not display unavailable tiles 506C and 506D. In other examples, unavailable tiles 506C and 506D may be grayed-out or displayed through some other means to indicate to caller 110 that the unavailable tiles 506C and 506D are currently unavailable. In some examples, user interface 500E may display, in response to caller 110 selecting a tile 506, a portion of the information received by caller device 112 from monitoring system 109. Monitoring system 109 may determine the amount of information received by caller device 112 that user interface 500E may display based on the severity of the unresponsiveness of callee 116. Monitoring system 109 may determine the severity of the unresponsiveness of callee 116 based on wellbeing score 510, callee behavioral history, and/or outlier activity threshold of callee 116. For example, if monitoring system 109 determines that wellbeing score 510 of callee 116 correspond to a wellness label of "average" or better (e.g., "good", "excellent"), user interface 500E may display the wellbeing score graph 514 but may not display sharing option 512, wellbeing score 510, and/or additional health information option 516. While the user interface 500E of FIG. 9 only displays tiles 506A, 506B, and wellbeing score graph 514, other example user interfaces 500 may include other combinations of details (e.g., only showing wellbeing score 510) and tiles 506 corresponding to different levels of severity of unresponsiveness of callee 116.

Figure 10:
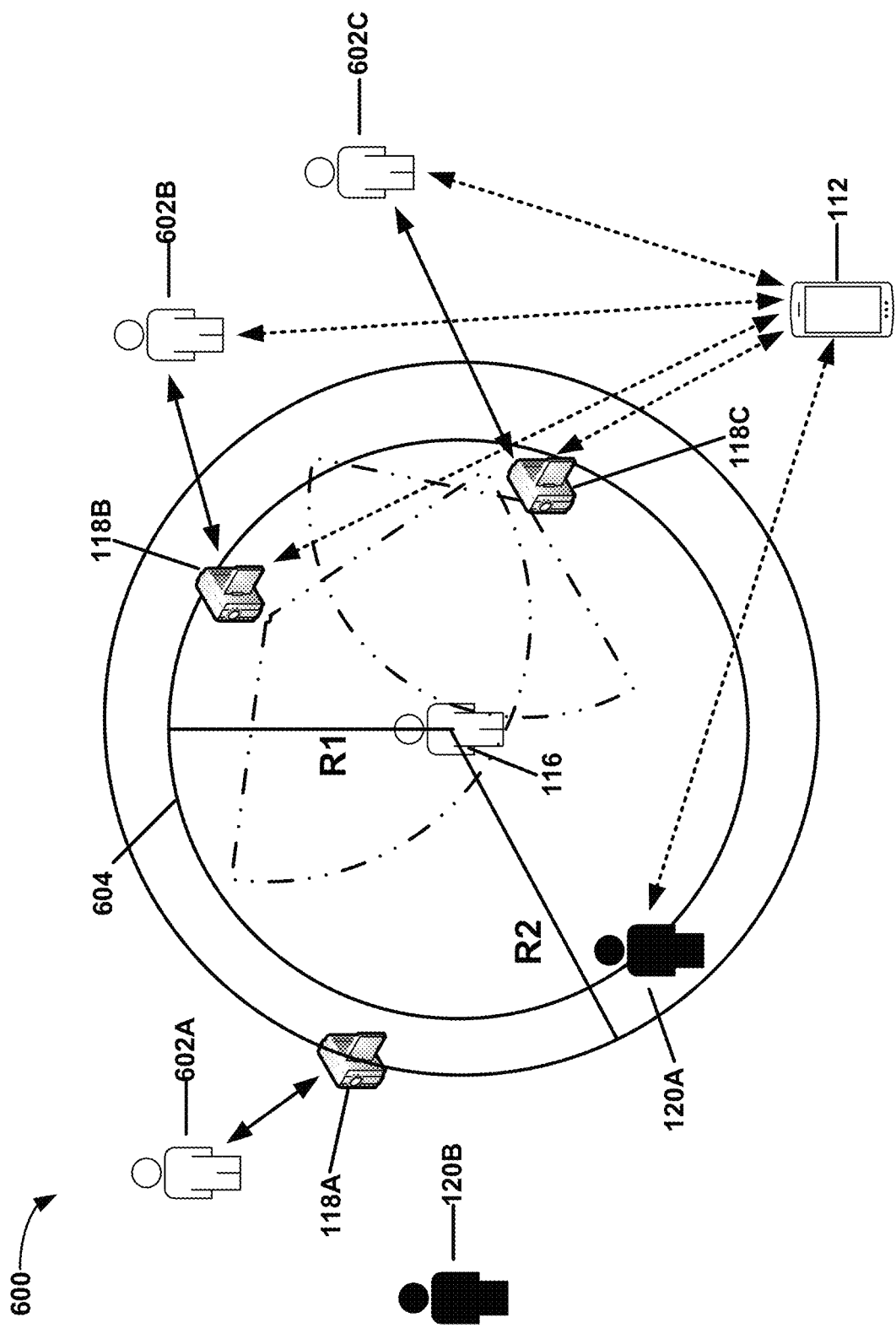
FIG. 10 is a conceptual diagram illustrating an example system in which a monitoring system may communicate with caller devices and network user devices and/or recording devices close to an unresponsive callee, in accordance with one or more techniques of this disclosure.

FIG. 10 is a conceptual diagram illustrating an example system 600 in which monitoring system 109 may communicate with caller devices 112 and network user devices 122 and/or recording devices 118 close to an unresponsive callee 116, in accordance with one or more techniques of this disclosure. Caller device 120 may communicate with recording devices 118A-C (collectively referred to as "recording devices 118") and network users 120A-B (collectively referred to as "network users 120") within the vicinity of callee 116 to aid in assessment of the status of callee 116. Monitoring system 109 may determine which recording devices 118 and network users 120 caller device 112 may communicate with based on which recording devices 118 and network users 120 are within a certain radius of user 116. In some examples, system 600 may be a computing system (e.g., computing system 102).

Monitoring system 109 may determine the position of callee 116 based on the location of callee device 114. The location of callee device 114 may be determined based on GPS locations, cell signal triangulation, and/or the location of a connected Wi-Fi signal.

Monitoring system 109 may initiate communications between recording devices 118 within a radius R1 of the location of callee device (recording device 118B, recording device 118C). Alternatively, caller device 112 may communicate directly with the recording devices 118 within the radius R1. The radius R1 may be determined based on the capabilities of the recording devices 118. While the diagram of FIG. 10 illustrates a same radius (R1) for all the recording devices 118, in other examples, monitoring system 109 may apply a different radius for each recording device 118 based on the individual capabilities of the devices 118. For example, monitoring system 109 may apply a longer radius for recording devices with a greater range than devices with shorter ranges. If a recording device is outside of the radius R1 (e.g., recording device 118A), monitoring system 109 may not initiate communications between the recording device 118A and caller device 112 and caller device 112 may not communicate directly with recording device 118A.

Monitoring system 109 may initiate communications between the owner/operator 602 of recording devices 118 and caller device 112 in accordance with some of the techniques discussed herein. For examples, monitoring system 109 may request permission from owner/operator 602 for caller device 112 to communicate with and receive feeds from recording device 118.

Monitoring system 109 may initiate communications between one or more network users 120 within a radius R2 (e.g., network user 120A) of callee 116 and the caller device 112. In other examples, caller device 112 may communicate directly with network users 120 within the radius R2. While the radius R2 is illustrated in FIG. 10 to be the same for all network users 120, in other examples the radius may vary between network users 120. For example, monitoring system 109 may assign a larger radius to a network user 120 with a car compared to a network user 120 who is on foot.

Figure 11:
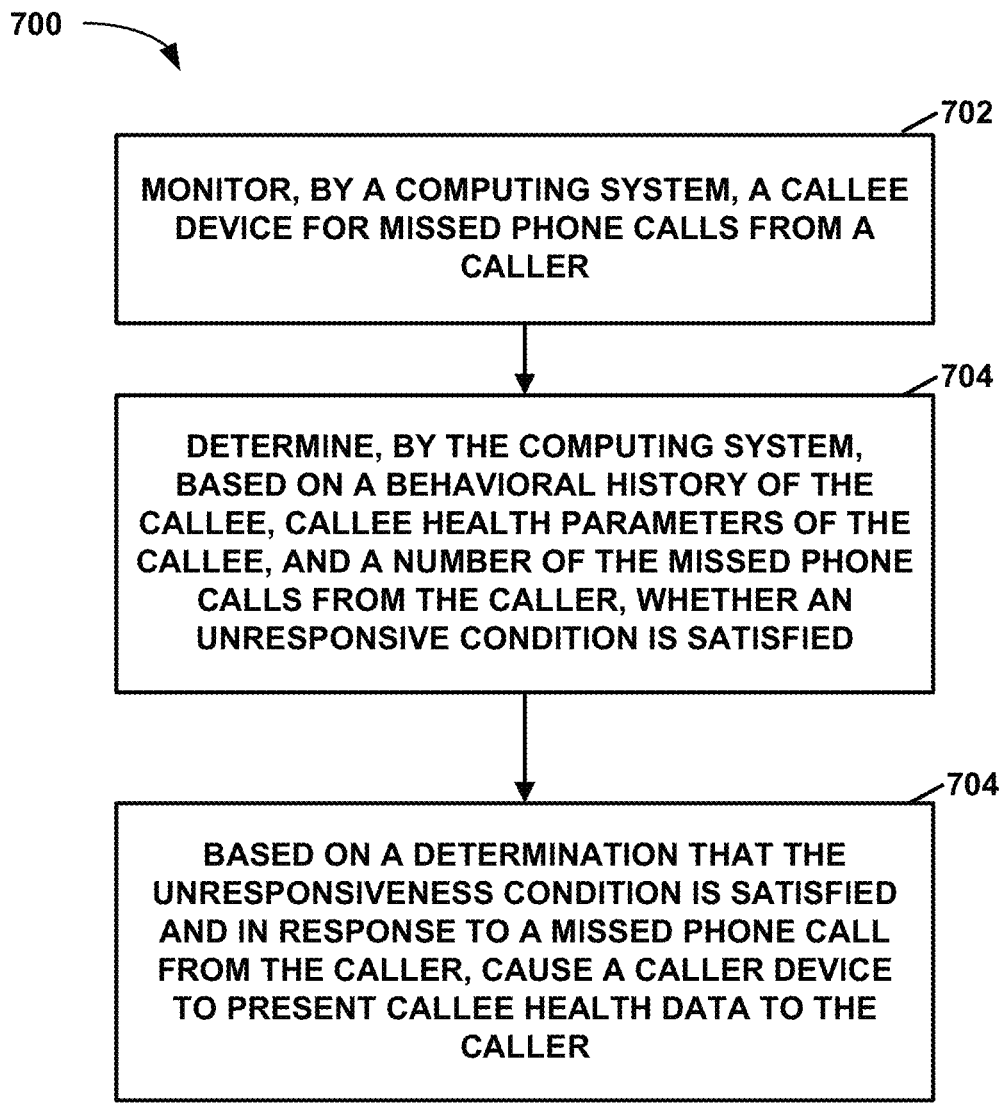
FIG. 11 is a flowchart illustrating another example callee monitoring method, in accordance with one or more techniques of this disclosure.

FIG. 11 is a flowchart illustrating another example callee monitoring method 700, in accordance with one or more techniques of this disclosure. A computing system (e.g., computing system 102) may perform the callee monitoring method 700. Computing system 102 may monitor a callee device 114 for missed phone calls from a caller 110 (702). The missed phone calls may be from caller device 112 of caller 110.

Computing system 102 may also determine, based on behavioral history of callee 116, callee health parameters of callee 116, and number of missed phone calls from caller 110, whether an unresponsiveness condition is satisfied (704). Computer system 102 may also, based on a determination that the unresponsiveness condition is satisfied and in response to a missed phone call from caller 110, cause caller device 112 to present callee health data to caller 110 (704).

The following is a non-limiting list of examples that may be in accordance with one or more techniques of this disclosure.

Example 1: A method comprising: monitoring, by a computing system, a callee device for missed phone calls from a caller; determining, by the computing system, based on a behavioral history of the callee, callee health parameters of the callee, and a number of the missed phone calls from the caller, whether an unresponsiveness condition is satisfied; and based on a determination that the unresponsiveness condition is satisfied and in response to a missed phone call from the caller, cause a caller device to prevent the callee health data to the caller.

Example 2: The method of example 1, wherein determining whether the unresponsiveness condition is satisfied comprises determining an outlier activity threshold in response to an incoming call based on the callee behavioral history and the callee health parameters, where the outlier activity threshold indicates that the callee is unresponsive and may require aid.

Example 3: The method of examples 1 or 2, wherein the method further comprises assigning weighted scores to each of a plurality of categories of the behavioral history of the callee and to each of the one or more callee health parameters; and determining a wellbeing score based on the weighted scores; and determining whether the unresponsiveness condition is satisfied comprises determining whether the unresponsiveness condition is satisfied based on the wellbeing score.

Example 4: The method of any of examples 1-3, further comprising: obtaining, by the computing system, the callee health parameters of the callee within a set period prior to and after each of the number of missed calls from the caller from one or more biometric devices.

Example 5: The method of any of examples 1-4, further comprising: obtaining, by the computing system, recorded data generated by one or more recording devices within a radius of the callee device; and transmitting, by the computing system, the recorded materials from the one or more recording devices to the caller device for display on the caller device.

Example 6: The method of any of examples 1-5, further comprising: identifying, by the computing system, a network user having a device that is within a radius of the callee device; and initiating, by the computing system, a communication session that includes the caller and the network user.

Example 7: The method of example 6, further comprising notifying the network user of a location of the callee device.

Example 8: The method of any of examples 1-7, where the callee health data comprises one or more callee current health metrics recorded by a biometric device.

Example 9: The method of example 8, wherein the callee health data further comprises activity history of the callee device for a set period prior to the one or more missed calls, where the activity history comprises application data from one or more applications on the callee device.

Example 10: The method of any of examples 1-9, further comprising: determining, by the computing system, an updated wellbeing score based on a change to the one or more health parameters; and sending, by the computing system, the updated wellbeing score to the caller device, where determining the updated wellbeing score comprises: obtaining, by the computing system, updated health parameters of the callee at a present time from one or more biometric devices and callee activity at the present time; determining, by the computing system, any changes between the health parameters and the updated health parameters; and determining, by the computing system, the updated wellbeing score based on the changes between the health parameters and the updated health parameters and the callee activity at the present time.

Example 11: The method of any of examples 1-10, further comprising notifying the callee, by the computing system, that the caller has been notified of the callee's health status.

Example 12: The method of any of examples 1-11, further comprising determining, by the computing system, an updated wellbeing score based on caller feedback, where the caller feedback comprises a determination by the caller that, based on the callee health data sent to the caller device associated with the caller, the unresponsiveness condition is not satisfied.

Example 13: A computing system comprising: a memory configured to store callee health parameters; and one or more processors implemented in circuitry, the one or more processors configured to: monitor a callee device for missed phone calls from a caller; determine, based on a behavioral history of the callee, the callee health parameters, and a number of the missed phone calls from the caller, whether an unresponsiveness condition is satisfied; and based on a determination that the unresponsiveness condition is satisfied and in response to a missed phone call from the caller, cause a caller device to present the callee health data to the caller.

Example 14: The system of example 13, wherein the one or more processors are configured, as part of determining whether the unresponsiveness condition is satisfied, to determine an outlier activity threshold in response to an incoming call based on the callee behavioral history and the callee health parameters, wherein the outlier activity threshold indicates that the callee is unresponsive and may require aid.

Example 15: The system of examples 13 or 14, wherein: the one or more processors are further configured to: assign weighted scores to each of a plurality of categories of the behavioral history of the callee and to each of the one or more callee health parameters; and determine a wellbeing score based on the weighted scores; and the one or more processors are configured, as part of determining whether the unresponsiveness condition is satisfied, to determine whether the unresponsiveness condition is satisfied based on the wellbeing score.

Example 16: The system of any of examples 13-15, wherein the computing system is further configured to: obtain recorded data generated by one or more recording devices is within a radius of the callee device; and transmit the recorded materials from the one or more recording devices to the caller device for display on the caller device.

Example 17: The system of any of examples 13-16, wherein the computing system is further configured to: identify a network user having a device that is within a radius of the callee device; and initiate a communication session that includes the caller and the network user.

Example 18: The system of any of examples 13-17, where the callee health data comprises activity history of the callee device for a set period prior to the one or more missed calls, where the activity history comprises application data from one or more applications of the callee device.

Example 19: The system of any of examples 13-19, wherein the one or more processors are further configured to: determine an updated wellbeing score based on a change to the one or more health parameters; and send the updated wellbeing score to the caller device, wherein the one or more processors are configured, as part of determining the updated wellbeing score, to: obtain updated health parameters of the callee at a present time from the one or more biometric devices and callee activity at the present time; determine any changes between the health parameters and the updated parameters; and determine the updated wellbeing score based on the changes between the health parameters and the updated health parameters and the callee activity at the present time.

Example 20: A non-transitory computer readable medium comprising instructions that, when executed, cause processing circuitry of a computing system to: monitor a callee device for missed phone calls from a caller; determine, based on a behavioral history of the callee, callee health parameters of the callee, and a number of missed calls from the caller, whether an unresponsiveness condition is satisfied; and based on a determination that the unresponsiveness condition is satisfied and in response to a missed phone call from the caller, cause a caller device to present callee health data to the caller.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, "Device" or "devices" (e.g., caller device 112, callee device 114, network user device 122) may include a plurality of hardware appliances configured to receive telecommunications from one or more other parties. The hardware appliances include, but are not limited to, cellphones, smartphones, tablets, laptops, personal computers, smartwatches. In other examples, "Device" or "devices" may include the use of a browser to communicate with one or more other devices.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage medium which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASIC s), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some respects, the functionality described herein may be provided within dedicated hardware and/or software modules. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

What is claimed is:

1. A computer-implemented method comprising:
monitoring, by one or more processors of a computing system, a callee device corresponding to a callee for missed phone calls from a caller;
assigning, by the one or more processors, weighted scores to each of a plurality of categories of a behavioral history of the callee and to each of one or more callee health parameters of the callee;
determining, by the one or more processors, a score of the callee based on the weighted scores;
determining, by the one or more processors, based on a number of the missed phone calls from the caller and the score of the callee, whether an unresponsiveness condition is satisfied; and
based on a determination that the unresponsiveness condition is satisfied and in response to a missed phone call from the caller to the callee, causing, by the one or more processors, a caller device to present callee health data to the caller.

2. The computer-implemented method of claim 1, wherein determining whether the unresponsiveness condition is satisfied comprises determining, by the one or more processors, an outlier activity threshold in response to an incoming call based on the behavioral history of the callee and the one or more callee health parameters, wherein the outlier activity threshold indicates that the callee is unresponsive and may require aid.

3. The computer-implemented method of claim 1, further comprising, obtaining, by the one or more processors, from one or more biometric devices, the one or more callee health parameters of the callee within a set period prior to and after each of the missed phone calls from the caller.

4. The computer-implemented method of claim 1, further comprising:
obtaining, by the one or more processors, recorded data generated by one or more recording devices within a radius of the callee device; and
transmitting, by the one or more processors, the recorded data from the one or more recording devices to the caller device for display on the caller device.

5. The computer-implemented method of claim 1, further comprising:
identifying, by the one or more processors, a network user having a device that is within a radius of the callee device; and
initiating, by the one or more processors, a communication session that includes the caller and the network user.

6. The computer-implemented method of claim 5, further comprising notifying, by the one or more processors, the network user of a location of the callee device.

7. The computer-implemented method of claim 1, where the callee health data comprises one or more callee current health metrics recorded by a biometric device.

8. The computer-implemented method of claim 7, wherein the callee health data further comprises an activity history of the callee device for a set period prior to the missed phone calls, where the activity history comprises application data from one or more applications on the callee device.

9. The computer-implemented method of claim 1, further comprising:
determining, by the one or more processors, an updated score based on a change to at least one of the one or more callee health parameters; and sending, by the one or more processors, the updated score to the caller device, wherein determining the updated score comprises:

obtaining, by the one or more processors, one or more updated callee health parameters of the callee at a present time from one or more biometric devices and a callee activity at the present time;

determining, by the one or more processors, any changes between the one or more callee health parameters and the one or more updated callee health parameters; and determining, by the one or more processors, the updated score based on the changes between the one or more callee health parameters and the one or more updated callee health parameters and the callee activity at the present time.

10. The computer-implemented method of claim 1, further comprising notifying the callee, by the one or more processors, that the caller has been notified of the callee health data.

11. The computer-implemented method of claim 1, further comprising determining, by the one or more processors, an updated score based on caller feedback, where the caller feedback comprises a determination by the caller that, based on the callee health data presented by the caller device to the caller, the unresponsiveness condition is not satisfied.

12. A computing system comprising:

at least one non-transitory memory configured to store one or more callee health parameters of a callee; and one or more processors implemented in circuitry, the one or more processors configured to:

monitor a callee device corresponding to the callee for missed phone calls from a caller;

assign weighted scores to each of a plurality of categories of a behavioral history of the callee and to each of the one or more callee health parameters of the callee;

determine a score of the callee based on the weighted scores;

determine, based on a number of the missed phone calls from the caller and the score of the callee, whether an unresponsiveness condition is satisfied; and based on a determination that the unresponsiveness condition is satisfied and in response to a missed phone call from the caller to the callee, cause a caller device to present callee health data to the caller.

13. The computing system of claim 12, wherein the one or more processors are configured, as part of determining whether the unresponsiveness condition is satisfied, to determine an outlier activity threshold in response to an incoming call based on the behavioral history of the callee and the one or more callee health parameters, wherein the outlier activity threshold indicates that the callee is unresponsive and may require aid.

14. The computing system of claim 12, wherein the one or more processors are further configured to:

obtain recorded data generated by one or more recording devices within a radius of the callee device; and transmit the recorded data from the one or more recording devices to the caller device for display on the caller device.

15. The computing system of claim 12, wherein the one or more processors are further configured to:

identify a network user having a device that is within a radius of the callee device; and initiate a communication session that includes the caller and the network user.

16. The computing system of claim 12, where the callee health data comprises an activity history of the callee device for a set period prior to the missed phone calls, where the activity history comprises application data from one or more applications on the callee device.

17. The computing system of claim 12, wherein the one or more processors are further configured to:

determine an updated score based on a change to at least one of the one or more callee health parameters; and send the updated score to the caller device, wherein the one or more processors are configured, as part of determining the updated score, to:

obtain one or more updated callee health parameters of the callee at a present time from one or more biometric devices and a callee activity at the present time;

determine any changes between the one or more callee health parameters and the one or more updated callee health parameters; and determine the updated score based on the changes between the one or more callee health parameters and the one or more updated callee health parameters and the callee activity at the present time.

18. One or more non-transitory computer readable media comprising instructions that, when executed by one or more processors, cause the one or more processors to:

monitor a callee device corresponding to a callee for missed phone calls from a caller;

assign weighted scores to each of a plurality of categories of a behavioral history of the callee and to each of one or more callee health parameters of the callee;

determine a score of the callee based on the weighted scores;

determine, based on and a number of the missed phone calls from the caller and the score of the callee, whether an unresponsiveness condition is satisfied; and based on a determination that the unresponsiveness condition is satisfied and in response to a missed phone call from the caller to the callee, cause a caller device to present callee health data to the caller.

* * * * *